(12) United States Patent
Noujeim

(10) Patent No.: US 7,894,878 B2
(45) Date of Patent: Feb. 22, 2011

(54) ANATOMICALLY-REFERENCED FIDUCIAL MARKER FOR REGISTRATION OF DATA

(75) Inventor: Marcel E. Noujeim, San Antonio, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 1455 days.

(21) Appl. No.: 11/323,349

(22) Filed: Dec. 30, 2005

(65) Prior Publication Data

US 2006/0241406 A1 Oct. 26, 2006

Related U.S. Application Data

(60) Provisional application No. 60/640,644, filed on Dec. 30, 2004.

(51) Int. Cl.
*A61B 5/05* (2006.01)
(52) U.S. Cl. .................. 600/426; 600/407; 600/414; 600/417; 600/429; 606/130
(58) Field of Classification Search .......... 600/407, 600/426, 429; 606/130
See application file for complete search history.

(56) References Cited

U.S. PATENT DOCUMENTS

| 5,588,430 | A | 12/1996 | Bova et al. |
| 5,954,647 | A | 9/1999 | Bova et al. |
| 6,096,048 | A * | 8/2000 | Howard et al. ............. 606/130 |
| 6,459,927 | B1 | 10/2002 | Franklin et al. |
| 2004/0015176 | A1 | 1/2004 | Cosman |

\* cited by examiner

*Primary Examiner*—Brian Casler
*Assistant Examiner*—John F Ramirez
(74) *Attorney, Agent, or Firm*—Meyertons, Hood, Kivlin, Kowert & Goetzel, P.C.; Eric B. Meyertons

(57) ABSTRACT

An anatomical data registration device may include a dental device. The dental device may configurable to be subject-specific. A dental device may be positionable in a substantially fixed spatial relationship relative to a portion of the subject. An anatomical data registration device may include one or more radiopaque markers. At least one of the radiopaque markers may be positioned in the dental device. The radiopaque marker may be configured to facilitate alignment of two or more images of the portion of the subject. The data registration device may be positionable within a subject's mouth.

12 Claims, 4 Drawing Sheets

ANATOMICALLY-REFERENCED FIDUCIAL MARKER FOR REGISTRATION OF DATA

PRIORITY CLAIM

This patent application claims priority to U.S. Provisional Patent Application Ser. No. 60/640,644 entitled "ANATOMICALLY-REFERENCED FIDUCIAL MARKER FOR REGISTRATION OF DATA" filed on Dec. 30, 2004, the disclosure of which is hereby incorporated by reference.

BACKGROUND

1. Field of the Invention

The present invention generally relates to a system and method for registering data using an anatomically referenced system of markers. Embodiments of the invention relate to a bite plate comprising fiducial markers.

2. Description of Related Art

Since the discovery of X-rays in 1895, film has been the primary medium for capturing, displaying, and storing radiographic images. It is a technology that practitioners are the most familiar and comfortable with in terms of technique and interpretation. Digital radiography is the latest advancement in dental imaging and is slowly being adopted by the dental profession. Digital imaging incorporates computer technology in the capture, display, enhancement, and storage of direct radiographic images. Digital imaging offers some distinct advantages over film, but like any emerging technology, it presents new and different challenges for the practitioner to overcome.

Film-based imaging consists of X-ray interaction with electrons in the film emulsion, production of a latent image, and chemical processing that transforms the latent image into a visible one. As such, radiographic film provides a medium for recording, displaying, and storing diagnostic information. Film-based images are described as analog images. Analog images are characterized by continuous shades of gray from one area to the next between the extremes of black and white. Each shade of gray has an optical density (darkness) related to the amount of light that can pass through the image at a specific site. Film displays higher resolution than digital receptors with a resolving power of about 16 lp/mm. However, film is a relatively inefficient radiation detector and, thus, requires relatively high radiation exposure. The use of rectangular collimation and the highest speed film are methods that reduce radiation exposure, but these techniques are not practiced commonly in private dental offices. Chemicals are needed to process the image and are often the source of errors and retakes. The final result is a fixed image that is difficult to manipulate once captured.

Digital imaging is the result of X-ray interaction with electrons in electronic sensor pixels (picture elements), conversion of analog data to digital data, computer processing, and display of the visible image on a computer screen. Data acquired by the sensor is communicated to the computer in analog form. Computers operate on the binary number system in which two digits (0 and 1) are used to represent data. These two characters are called bits (binary digit), and they form words eight or more bits in length called bytes. The total number of possible bytes for 8-bit language is $2^8=256$. The analog-to-digital converter transforms analog data into numerical data based on the binary number system. The voltage of the output signal is measured and assigned a number from 0 (black) to 255 (white) according to the intensity of the voltage. These numerical assignments translate into 256 shades of gray. The human eye is able to detect approximately 32 gray levels. Some digital systems sample the raw data at a resolution of more than 256 gray values such as 10 bit or 12 bit values. The large number of gray values is reduced to 256 shades of gray with the advantage of controlling under or overexposed images.

Direct digital imaging systems produce a dynamic image that permits immediate display, image enhancement, storage, retrieval, and transmission of the image. Digital sensors are more sensitive than film and require significantly lower radiation exposure. Dynamic range or latitude is the range of exposures that will produce images within the useful density range. This corresponds to the straight-line portion of the Hurter and Driffield (H & D) curve or the characteristic curve. This curve demonstrates the relationship between exposure (number of X-rays) and optical density (darkness) of an image receptor. The scale of useful densities ranges from 0.6 (low density—light) to 3.0 (high density—dark). Beyond these parameters, the image is not diagnostic. Typically, the H & D curve for film has a stretched letter S appearance with the top curve known as the shoulder and the bottom curve the toe. Exposure changes in the shoulder (high exposure) and toe (low exposure) have little affect on density, but small changes in the straight-line portion between them significantly affect density. The more vertical the straight-line portion of the curve is, the smaller the range and the narrower the film latitude. In comparison, the dynamic range of charged coupled devices (CCDs) is linear with no shoulder or toe and is much wider than film.

For years users (e.g., dentists, surgeons, doctors) have dealt with the problem of no quantitative measures to determine the success of a particular treatment. For example, when evaluating bone height, changes can be masked by disparities in projection geometry. Digital subtraction radiography is a technique that allows quantitative determination in changes in radiographs. The premise is quite simple. A radiographic image is generated before a particular treatment is performed. At some time after the treatment, another image is generated. The two images are digitized and compared on a pixel-by-pixel basis. The resultant image shows only the changes that have occurred and "subtracts" those components of the image that are unchanged. The magnitude of the changes can then be measured by evaluating the histogram (graphic depiction of the distribution of gray levels) of the resultant image. If the exact projection geometry and receptor placement are not recreated, the changes in the subtracted image will demonstrate the effects of misregistration rather than the effects of a therapeutic intervention. Direct digital imaging has been a great help in the quest to take the technique of digital subtraction radiography out of the laboratory setting and actually use it clinically. Now that consistent file sizes can be achieved, the attention is being directed towards methods for recreating image receptor placement and projection geometry so dentistry can start to provide quantitative data about treatment outcomes.

One problem with digital subtraction radiography is acquiring images which are comparable. Comparable images include images, which are of essentially the same space, or area allowing registered data from separate images of the same space to be compared (e.g., subtracted). Currently acquiring comparable images is accomplished by repeatedly positioning a patient in a particular location and orientation relative to the medical apparatus on a number of separate occasions. For example, a patient may return on multiple days for radiation therapy (radiotherapy) in which a beam of radiation is directed toward a particular feature in the body (a "target") such as a cancerous tumor. One approach to targeting the same feature at each session is, at each session, to first restrain the patient relative to the apparatus and then to determine the location of the target relative to the apparatus, for example, using the locations of fiducial markers on a patient. This same approach is also used in acquiring digital images of a patient using for example a CT scanner. In one approach, a "bite plate" with trackable markers is used to determine the position of the patient relative to a medical apparatus using a remote sensing system. The medical apparatus is adjusted according to the sensed position of the patient: Another approach to targeting the same feature at each session is to restrain the patient in precisely the same position relative to the apparatus at each session. In one such approach, a complex, cumbersome, and often-painful positioning device, such as a stereotactic head frame, is fixed to a patient prior to scanning. The device is left in place after scanning to later position or register the patient in the medical apparatus. In another approach to repeatable positioning, a molded synthetic cast of a patient's head is made, and split in half to allow removal and subsequent re-attachment to the head. A stereotactic frame is attached to the mold, thereby allowing repeatable positioning of the stereotactic frame. Features in the body are then targeted relative to the stereotactic frame. Current methods have several associated disadvantages. For example, current methods may increase a patient's discomfort by increasing the length of time required to perform a CT scan or some other procedure. Current methods typically employ large and cumbersome systems coupled to a patient. Systems may be temporarily positionable in a portion of a patient. Systems may be temporarily coupled to a patient resulting in further discomfort. The current invention is designed to overcome disadvantages and shortcomings of current methods and systems.

SUMMARY

In some embodiments, an anatomical data registration device ("registration device") may include a dental device. The dental device may be calibrated to be subject-specific. Upon configuration of the dental device relative to at least a portion of a subject, the dental device may be positionable in a substantially fixed spatial relationship relative to a portion of the subject. An anatomical data registration device may include one or more radiopaque markers. At least one of the radiopaque markers may be positioned in the dental device. The radiopaque marker may be configured to facilitate alignment of two or more images of the portion of the subject. The data registration device may be positionable within a subject's mouth.

In some embodiments, a registration device may function to allow a subject/patient freedom of movement when positioned in the subject's mouth.

In some embodiments, a registration device may include a grasping device coupled to the dental piece. At least a portion of the grasping device may extend out of a subject's mouth when the dental piece is positioned in the subject's mouth such that the grasping device facilitates removal of the dental piece from the subject's mouth.

In some embodiments, a registration device may include three or more radiopaque markers. In some embodiments, a radiopaque marker may include a radiopaque plate. In some embodiments, at least one of the radiopaque markers may function to facilitate alignment of two or more images of the portion of the subject at a time after obtaining the images In some embodiments, a registration device may include a dental piece. The dental piece may include a bite plate. The dental piece may function to be reproducibly positioned in the subject's mouth.

BRIEF DESCRIPTION OF THE DRAWINGS

Advantages of the present invention will become apparent to those skilled in the art with the benefit of the following detailed description of embodiments and upon reference to the accompanying drawings detailed below.

Figure 1:
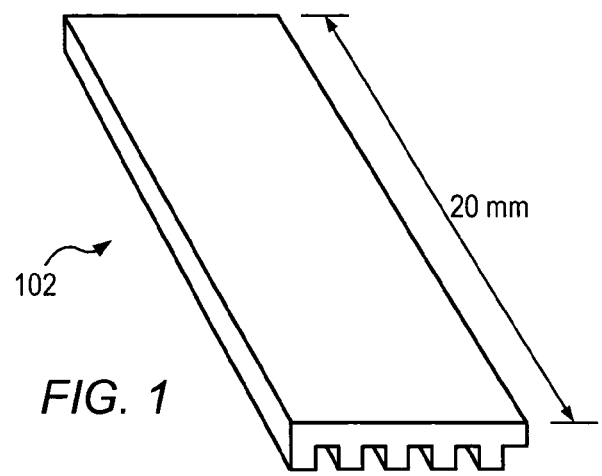
FIG. 1. depicts a perspective view of an embodiment of a radiopaque marker.

While the invention is susceptible to various modifications and alternative forms, specific embodiments thereof are shown by way of example in the drawings and will herein be described in detail. The drawings may not be to scale. It should be understood that the drawings and detailed description thereto are not intended to limit the invention to the particular form disclosed, but to the contrary, the intention is to cover all modifications, equivalents and alternatives falling within the spirit and scope of the present invention as defined by the appended claims.

DETAILED DESCRIPTION OF EMBODIMENTS

Referring to the drawings an anatomical data registration device is designated generally by reference numeral 100. Registration device 100 may be used in conjunction with, for example, a CT scanning instrument. The registration device may be used as or include one or more fiducial markers. The registration device may function to serve as a reference for a physical coordinate system. A physical coordinate system is usually obtained by mapping or registering a coordinate system of a scanned image to a physical coordinate system. Subsequent scans taken at a different time or using a different technique may be registered to a common physical coordinate system in order to view the same features in the different scanned images. Registration is generally defined as the act of adjusting something to match a standard.

Typically fiducial markers are currently used in combination with other systems to assist in positioning a patient relative to a medical apparatus during a procedure. The fiducial markers may allow a patient or at least a portion of a patient to be accurately and repeatably positioned in a fixed position relative to a medical apparatus.

U.S. Pat. No. 5,954,647 to Bova et al. ("Bova"), which is incorporated by reference as if fully set forth herein, describes a marker system and related stereotactic procedure. The marker system may be described as a system for medical procedures, the system including a locator attachable to a patient, having at least 3 LEDs thereon, and having a registration portion for registration with a portion of a patient's body. The registration portion allows removal of the locator from the patient and re-attachment to the patient with an identical orientation relative to the portion of the patient that the locator was previously attached. The system has a positioner independent of the locator and operable to secure at least the portion of the patient in a desired position. A sensing subsystem is operable for sensing the positions of the LEDs when the patient is in the desired position. The locator is non-invasive. The locator is more specifically a bite plate with an external portion connected thereto. The LEDs are positioned on the external portion. The bite plate has dental impression material for fabrication of a mold to bring the bite plate in registry with teeth of the patient. The mold is operable to bring the bite plate in registry with teeth of the patient with an identical orientation relative to the teeth as when the bite plate was previously attached. Bova's device requires extending the necessary period of time for performing a CT scan on a subject due to the added step of positioning the patient using the LEDs as a reference point before scanning the subject.

Current methods (e.g., Bova's method) may increase a patient's discomfort by increasing the length of time required to perform a CT scan or some other procedure. Current methods typically employ large and cumbersome systems coupled to a patient. Systems may be temporarily positionable in a portion of a patient. Systems may be temporarily coupled to a patient resulting in further discomfort.

In some embodiments, registration device 100 may be positionable within a patient. The registration device may be positionable within an existing opening or cavity of a patient. For example the registration device may be positionable within the mouth of a patient. In some embodiments, a registration device may be entirely positionable within a patient's mouth. A registration device small enough to fit entirely within a patient's mouth may provide advantages such as increased comfort relative to current registration systems. Once the registration device is positioned it may allow total freedom of movement.

Depending upon what portion of a patient's body a user wishes to scan or image, the patient need not be positioned relative to the instrument in the same position every time. Even different portions of a patient need not be positioned relative to each other in the same position every time. For example when a user wishes to acquire a CT scan of a portion of a patient's teeth the spatial relationship of the rest of the patient's body relative to the patient's teeth is substantially inconsequential from scan to scan.

In some embodiments, a position of different portions of a patient may need to be positioned relative to each other in substantially the same position for multiple scans. For example when a registration device is positioned in a patient's mouth when, for example, a user wishes to obtain multiple scans of a portion of a patient's shoulder, the patient's shoulder must be positioned in the same manner relative to the patient's mouth and the registration device over the course of the multiple scans. Additional devices may be employed to stabilize and/or mark the position of one portion of a patient's body relative to another portion of a patient's body. For example a patient may lie on a table and one or more restraints may be employed to ensure two or more portions of a patient's body remain spatially fixed relative to one another.

In some embodiments, a registration device may include a grasping mechanism. A grasping mechanism may function to allow a user to more easily remove the registration device from a patient's cavity. The grasping device may be coupled to the registration device. The grasping device may be semi-flexible. The grasping device may be flexible in order to lessen the chance of a patient being injured by the grasping device.

In some embodiments, a registration device may be formed at least in part with pliable materials. Pliable materials may be generally defined as a material which upon applying sufficient pressure to deform the pliable material from a first shape to a second shape the pliable material retains the second shape. For example the registration device may be formed from plastics. Plastics used to form at least a portion of the registration device may deform under pressure. Forming the registration device of pliable materials may allow the registration device to be adaptable to be patient specific. For example a user may insert all or a portion of the registration device into a patient's mouth. Upon insertion, the patient may bite down upon the registration device. Biting down upon the registration device may leave impressions of the patient's teeth upon the surface of the registration device. Dental impressions upon the surface of the registration device may be used to reposition the registration device in the patient's mouth at a later time in the same position the registration device was originally placed.

A registration device may be formed from other pliable materials allowing impressions to be formed in the surface of the registration device. In some embodiments, impressions of a portion of a patient may be taken using methods known to one skilled in the art. From these impressions a mold may be formed to use to manufacture a patient specific registration device. In some embodiments, a registration device may be formed from a pliable material that deforms when pressure is applied but which hardens under proper conditions (e.g., heat, ultraviolet light). For example, a device may be formed from a pliable which loses elasticity upon exposure to heat and/or light (e.g., ultraviolet light). A radiopaque marker may be positioned in the device at a point before and/or after impressions have been formed in the registration device. A radiopaque marker may be positioned in the device at a point before and/or after the pliable material has been transformed into a nonpliable material.

For example, a registration device may be designed to be positioned within the oral cavity of a patient. The registration device may be positioned within the oral cavity of the patient. The registration device may function such that a patient has freedom of movement when positioned in the subject's mouth (except for possibly a patient's lower jaw). The patient may upon direction apply pressure to the registration device by biting the registration device. By biting the registration device the patient may imprint a pattern specific for their teeth. A first image may be acquired at this time, or a later time, to be used as a baseline or standard. The image may be acquired of a portion of the patient within a close proximity to the position of the registration device. The image may be acquired of a portion of the patient that is substantially spatially fixed relative to the position of the registration device when the registration device is positioned within the patient's oral cavity.

In some embodiments, an image may be acquired of a portion of the patient that is not naturally spatially fixed relative to the position of the registration device when the registration device is positioned within the patient's oral cavity. In this example other systems may be necessary to record and/or inhibit the movement of the portion of the patient relative to the registration device when the registration device is positioned within the patient's oral cavity.

At a later time (e.g., after a medical procedure) one or more second images (e.g., post-operative images) may be acquired. A CT scanner may be used to acquire the images. The registration device may be repositioned in the patient's oral cavity in substantially the same spatial relationship as the registration device was previously positioned. The impressions previously formed in the surface of the registration device by the patient may be used to assist in orienting and positioning the registration device within the patient's oral cavity.

The acquired images may be digital images. Acquiring images in a digital format may allow the images to be manipulated more easily. For example digital images may be more easily compared to one another in a quantitative manner. In some embodiments, the first and second digital images may be used for techniques such as digital subtraction radiography. If necessary non-digital images may be digitized for the purposes of subjecting them to digital subtraction. The first and second images may be compared on a pixel-by-pixel basis. The resultant image shows only the changes that have occurred and "subtracts" those components of the image that are unchanged.

Figure 2:
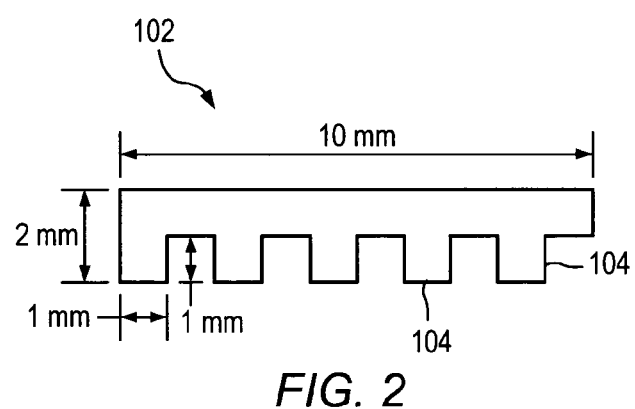
FIG. 2. depicts an end view of an embodiment of a radiopaque marker.

In some embodiments, registration device 100 may include one or more radiopaque markers 102. FIG. 1 depicts a perspective view of an embodiment of a radiopaque marker. FIG. 2 depicts an end view of an embodiment of a radiopaque marker. A radiopaque marker may be composed of radiopaque materials. Radiopaque materials may include any materials that are relatively impenetrable by x-rays or other forms of radiation. In some embodiments, a radiopaque marker may be formed from non-radiopaque materials, but may include patterns, markings, and/or indicia formed from radiopaque materials.

Radiopaque markings may be applied to the radiopaque marker in a wide variety of methods. For instance, if the radiopaque marker is formed from/covered in a woven fabric, then radiopaque threads could be woven into the fabric at regular intervals. Radiopaque materials may include metal (e.g., alloys of gold, nitinol, platinum, or stainless steel). Radiopaque markers may be formed from polymeric material mixed with a radiopaque material, such as a metal powder (e.g., barium sulfate). Radiopaque markers may be formed from biocompatible materials. Radiopaque markings could also be imprinted onto the radiopaque marker with radiopaque ink. Such ink is available from CI Inc. (Norton, Mass.).

In some embodiments, radiopaque markers may be marked using chemical vapor deposition, physical vapor deposition, electroplating, and/or ion-beam assisted deposition. In ion-beam assisted deposition, an electron beam evaporator is used to create a vapor of atoms that coats the surface of the material.

Some radiopaque materials might interfere with certain scanning techniques because certain scanning techniques are extremely sensitive to metal and metal can substantially mask certain signals. However, if metal markings are made sufficiently small, they will show as bands in certain scans. Using metal fibers 0.1 mm to 0.05 mm to create a pattern by weaving into a radiopaque marker may make the radiopaque marker viewable. A metal may be applied to the radiopaque marker by ion deposition that can deposit a layer of metal 0.01 mm thick. Small tubular strands filled with fatty acids could also be used as MRI sensitive markings. Such strands may be applied to a radiopaque marker.

In some embodiments, markings may be Positron Emission Tomography ("PET") sensitive by making the markings slightly radioactive. Such markings would probably only be useful for a relatively short time frame after the procedure because of radioactive decay. Markings (e.g., metal threads) may also be attached to the material by adhesive means, such as a biocompatible glue. Biocompatible glues are available from Cryolife Inc. (e.g., Bioglue) (Kennesaw, Ga.) or Cyanoacrylate, by Loctite Corp. (Rocky Hill, Conn.).

In some embodiments, markings may be arranged in a pattern. The pattern may be such so as to allow alignment of at least a portion of two or more digital images in at least two-dimensions. The pattern may be such so as to allow alignment of at least a portion of two or more digital images in at least three-dimensions. Patterns may include a series of equally spaced substantially parallel lines. Patterns may include a grid of substantially parallel lines. Patterns may include concentric circles and/or a series of lines radiating from a single point at a set angle apart.

In some embodiments, faces/sides of a marker may be distinguishable from one another due to different three-dimensional patterns formed in the surface and/or indicia inscribed in or on the marker using radiopaque materials.

In some embodiments, a radiopaque marker may include a polymer that is coated, compounded, filled, loaded, or mixed with a radiopaque substance such as iodide, iodine, zirconium oxide, barium sulfate, bismuth trioxide, and/or a related oxide or salt substance. Composite radiopaque materials may contain at least one element having an atomic number, higher than about 22. Radiopaque materials may include, but are not limited to, gold, platinum, tantalum, metallic biomaterial alloys for coating, and small particles of these materials, preferably, less than 10 microns in size for compounding.

In some embodiments, a radiopaque marker may be formed in a predetermined shape. The shape may be such so as to allow alignment of at least a portion of two or more digital images in at least two-dimensions. The shape may be such so as to allow alignment of at least a portion of two or more digital images in at least three-dimensions. The radiopaque marker may serve as a reference point with which to align two or more digital images.

In some embodiments, combinations of marking methods described herein (or related methods described elsewhere) may be combined in the formation of the radiopaque marker.

In some embodiments, a radiopaque marker may be formed of biocompatible materials. The radiopaque marker may be formed of biocompatible materials for increased safety to the patient. Forming the radiopaque marker from biocompatible materials may decrease any likelihood of exposing a patient to potentially harmful materials. In some embodiments, a radiopaque maker may be formed from materials that are not biocompatible or it is unknown what the particular biocompatibility of the material is. This may however not pose a problem as long as the radiopaque marker is enclosed within a biocompatible material. A biocompatible material may be formed around the radiopaque marker. A biocompatible coating may be applied to the exterior surface of the radiopaque marker. The material of the registration device that the radiopaque marker is embedded within may be formed from biocompatible materials effectively insulating the radiopaque marker from the patient.

FIG. 1 depicts a perspective view of an embodiment of radiopaque marker 102. FIG. 2 depicts an end view of an embodiment of radiopaque marker 102. The radiopaque marker depicted in FIG. 1 and FIG. 2 is but one example of an embodiment of a shape of a radiopaque marker.

The radiopaque marker embodiment depicted in FIG. 1 and FIG. 2 may include ridges 104 or teeth running down the length of the body of the radiopaque marker. The ridges may serve as an alignment facilitator to align a portion of two or more images. The ridges may assist a user in determining the orientation of the radiopaque marker relative to a portion of a patient. The ridges may assist a user in determining the orientation of a portion of a patient relative to the known orientation of the radiopaque marker.

In some embodiments, a radiopaque marker may be formed to specific and/or exacting tolerances. For example the radiopaque marker depicted in FIG. 1 and FIG. 2 is 20 mm long by 10 mm wide by 2 mm thick. The dimensions of the radiopaque marker may be controlled within very tight specifications. Advantages of controlling and/or knowing the exact dimensions of a radiopaque marker may include allowing a user who knows the exact dimensions of the radiopaque marker to use the radiopaque marker as a reference scale when viewing digital images of the radiopaque marker positioned within a patient.

The radiopaque marker may be sized to any appropriate dimension. Appropriate dimensions for the radiopaque marker may be determined by a user based on, for example, where the radiopaque marker will be positioned relative to the patient. Other factors may affect the necessary dimensions of the radiopaque marker including, but not limited to, total area that the user is interested in scanning such that the radiopaque marker extends through the entire area of interest to be scanned so the radiopaque marker may be used as a reference point throughout the area of interest.

The size and/or shape of a cavity may determine the eventual size and/or shape of the radiopaque marker. For example a small child may require a smaller radiopaque marker than an adult subject may require.

The radiopaque marker depicted in FIG. 1 and FIG. 2 is merely one embodiment of a radiopaque marker and should not be seen in any way as limiting as far as the size and/or shape which a radiopaque marker may assume. A radiopaque marker may assume any number of shapes and/or sizes.

Features such as ridges 104 may extend the entire length/width of radiopaque marker 102. Advantages for extending a feature (e.g., ridges 104) along the entire length/width of the radiopaque marker may be advantageous. One advantage may include the fact that many scanning instruments acquire images of a portion of a patient by taking images of consecutive two-dimensional slices of the portion. Features extending along the entire length/width of the radiopaque marker may facilitate alignment of two or more images no matter what image slice is being studied because the feature will be evident no matter what two-dimensional slice of the radiopaque marker is viewed.

In some embodiments, features of the radiopaque marker may include anything that will allow a user to align portions of two or more images. As depicted in FIG. 1 and FIG. 2 features may be repeated to provide a user multiple points of reference. Features, for example, may have straight edges to allow a user to more easily overlap features when comparing images. In some embodiments, rounded edges or features may be used. Features may be positioned on more than one face of the radiopaque marker.

Figure 3:
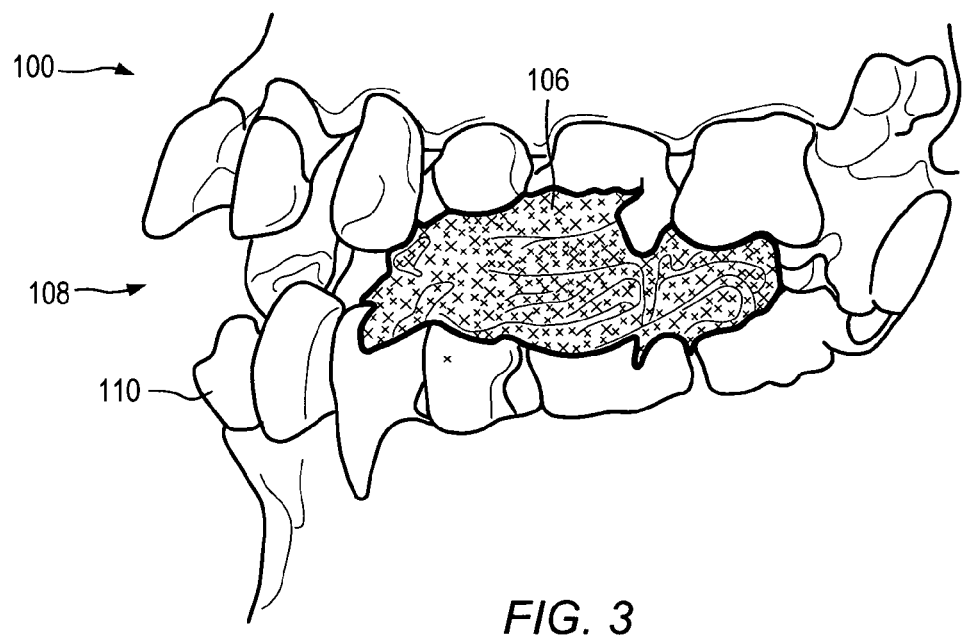
FIG. 3. depicts an embodiment of a dental piece positioned in a mouth of a patient.

In some embodiments, a registration device may be designed to be positioned within an oral cavity or mouth of a patient. The registration device may include a dental device 106 as depicted in FIG. 3-FIG. 9. FIG. 3 depicts an embodiment of a radiopaque marker embedded in a dental piece positioned in a mouth 108 of a patient.

Figure 4:
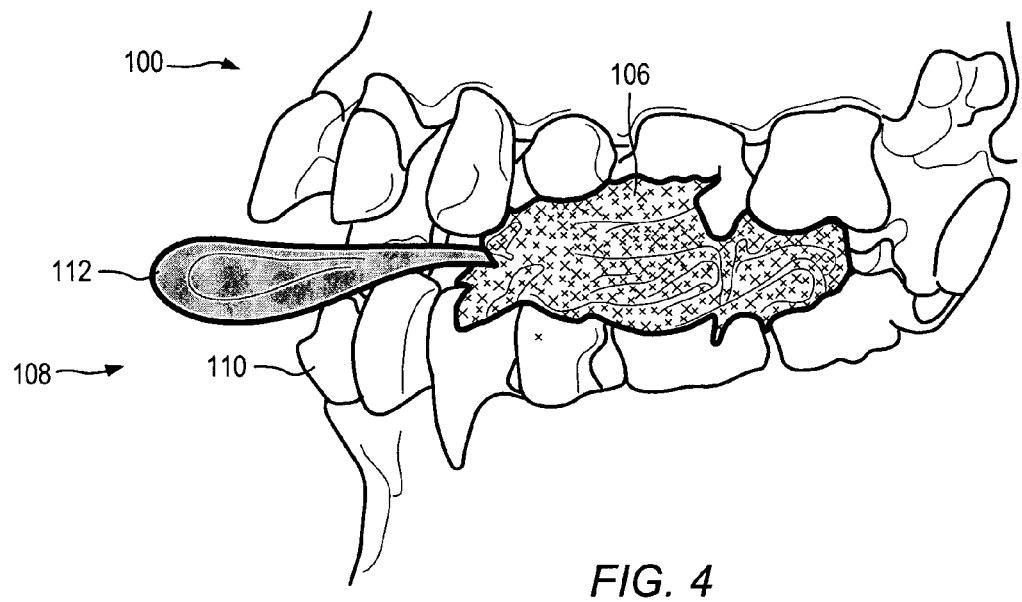
FIG. 4. depicts an embodiment of a dental piece positioned in a mouth of a patient including a grasping device coupled to the dental device.

In some embodiments, a registration device may include a grasping mechanism. A grasping mechanism may function to allow a user to more easily insert and/or remove the registration device from a patient's cavity. The grasping device may be coupled to the registration device. The grasping device may be semi-flexible. The grasping device may be flexible in order to lessen the chance of a patient being injured by the grasping device. FIG. 4 depicts an embodiment of a dental piece positioned in a mouth of a patient including a grasping device 112 coupled to the dental device.

Figure 5:
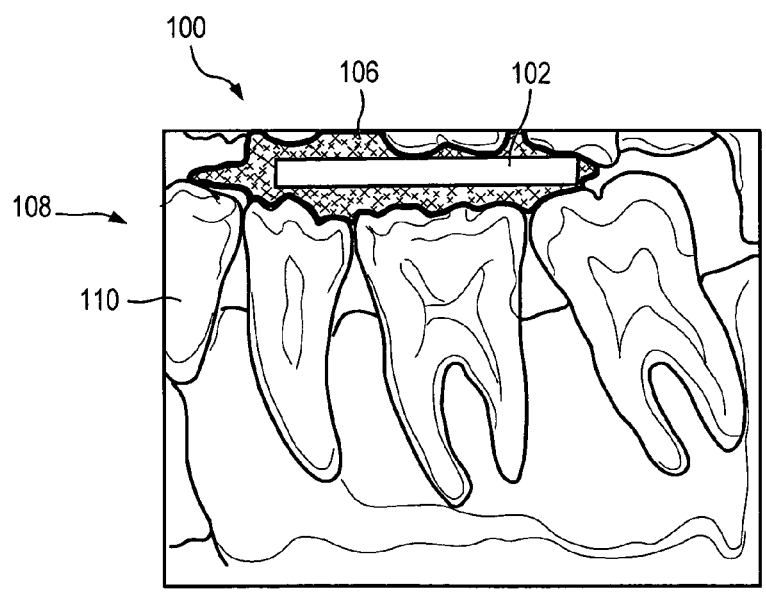
FIG. 5. depicts an embodiment of a baseline CT scan of a dental piece positioned in a mouth of a patient.
Figure 6:
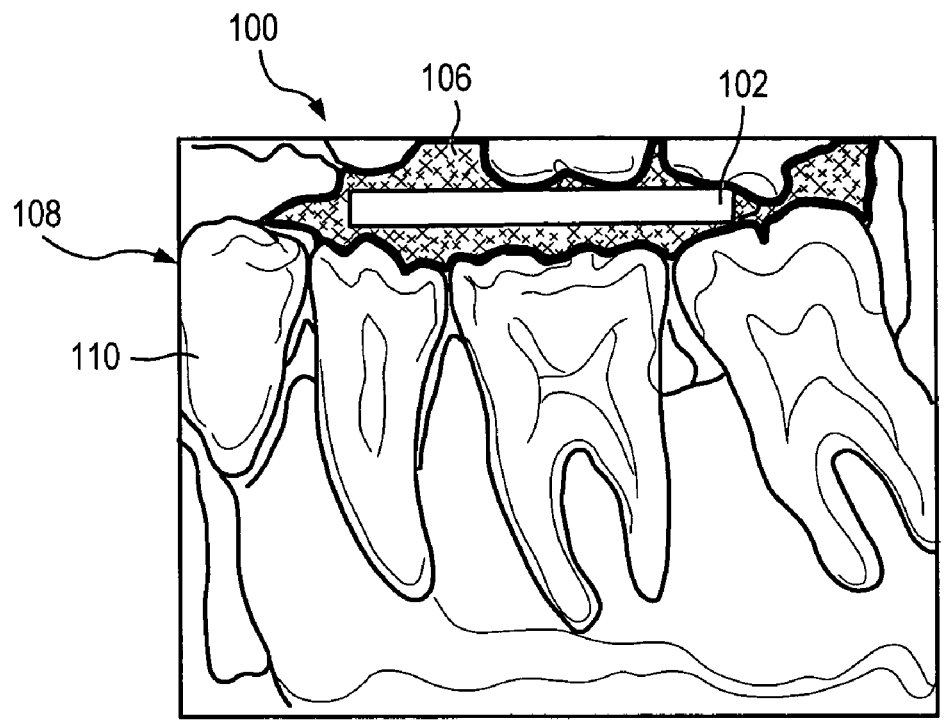
FIG. 6. depicts an embodiment of a post-operative CT scan of a dental piece positioned in a mouth of a patient.
Figure 7:
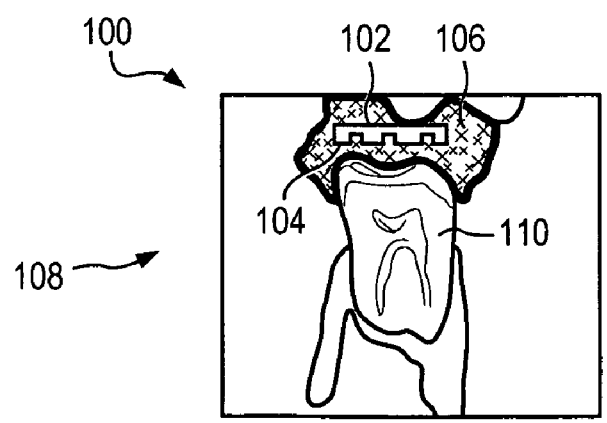
FIG. 7. depicts an embodiment of a baseline and a post-operative CT scan of a dental piece positioned in a mouth of a patient during digital subtraction.

FIG. 5 depicts an embodiment of a baseline CT scan of a dental piece positioned in a mouth 108 of a patient. FIG. 6 depicts an embodiment of a post-operative CT scan of a dental piece positioned in a mouth 108 of a patient. FIG. 7 depicts an embodiment of a baseline and a post-operative CT scan of a dental piece positioned in a mouth 108 of a patient during digital subtraction.

Figure 8:
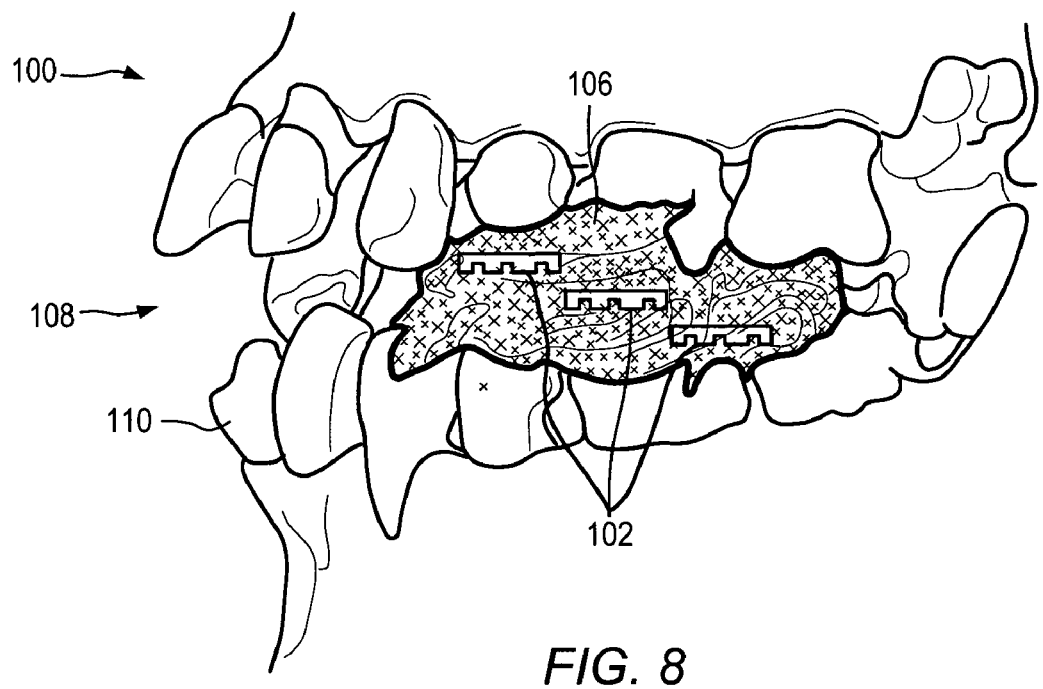
FIG. 8. depicts an embodiment of three radiopaque markers embedded in a dental piece positioned in a mouth of a patient.
Figure 9:
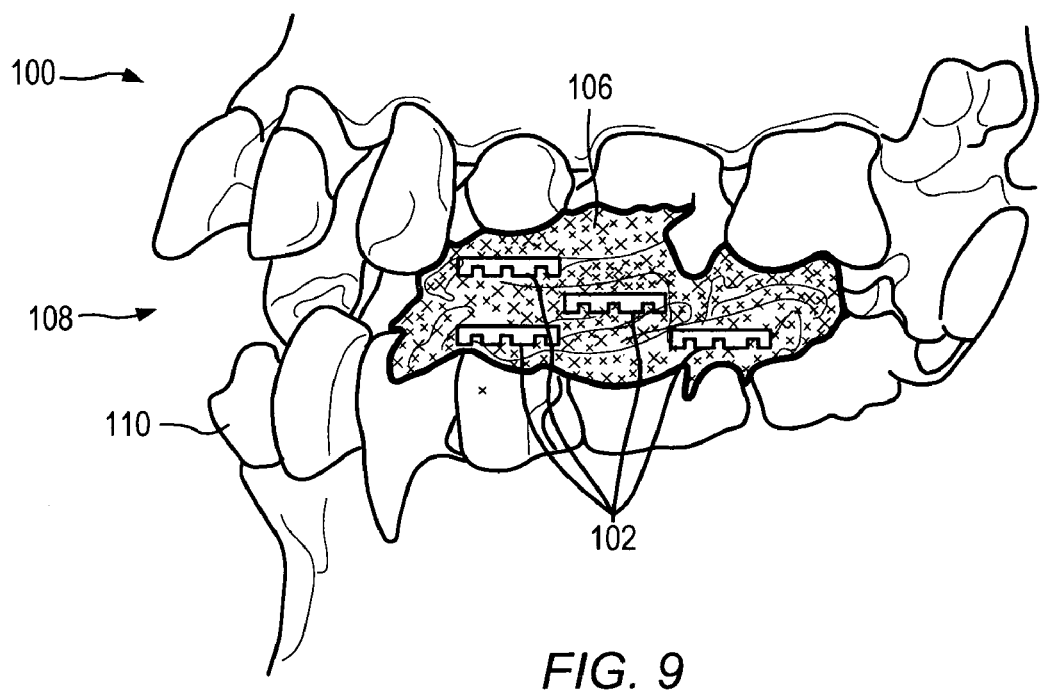
FIG. 9. depicts an embodiment of four radiopaque markers embedded in a dental piece positioned in a mouth of a patient.

In some embodiments, two or more radiopaque markers 102 may be embedded in dental device 106. In some embodiments, three or more radiopaque markers 102 may be embedded in dental device 106. In some embodiments, three radiopaque markers 102 may be embedded in dental device 106. Embedding multiple radiopaque markers in a dental device may assist in aligning two or more provided images. Embedding three or more radiopaque markers in a dental device may allow two or more provided images to be aligned in all three dimensions without using radiopaque markers with any specific shape by merely using the position of the three (or more) marker relative to one another. FIG. 8 depicts an embodiment of three radiopaque markers 102 embedded in a dental piece 106 positioned in a mouth 108 of a patient. FIG. 9 depicts an embodiment of four radiopaque markers 102 embedded in a dental piece 106 positioned in a mouth 108 of a patient.

In some embodiments, radiopaque marker 102 may be embedded in dental device 106. The dental device may be formed at least in part with pliable materials. For example the dental device may be formed from plastics. Plastics used to form at least a portion of the dental device may deform under pressure. Forming the dental device of pliable materials may allow the dental device to be adaptable to be patient specific. For example, a user may insert all or a portion of the dental device into a patient's mouth. Upon insertion, the patient may bite down upon the dental device. Biting down upon the dental device may leave impressions of the patient's teeth 110 upon the surface of the dental device. Dental impressions upon the surface of the dental device may be used to reposition the dental device in the patient's mouth at a later time in the same position the dental device was originally placed.

A dental device may be formed from other pliable materials allowing impressions to be formed in the surface of the dental device. In some embodiments, impressions of a portion of a patient may be taken using methods known to one skilled in the art. From these impressions a mold may be formed to use to manufacture a patient specific registration device. In some embodiments, a dental device may be formed from a pliable material that deforms when pressure is applied but which hardens when treated with proper conditions (e.g., heat, ultraviolet light).

In this patent, certain U.S. patents, U.S. patent applications, and other materials (e.g., articles) have been incorporated by reference. The text of such U.S. patents, U.S. patent applications, and other materials is, however, only incorporated by reference to the extent that no conflict exists between such text and the other statements and drawings set forth herein. In the event of such conflict, then any such conflicting text in such incorporated by reference U.S. patents, U.S. patent applications, and other materials is specifically not incorporated by reference in this patent.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. An anatomical data registration device, comprising:
a dental device configurable to be subject specific such that upon configuration, the dental device is positionable in a substantially fixed spatial relationship relative to a portion of the subject; and
one or more radiopaque markers positioned in the dental device, wherein at least one of the radiopaque markers is configured to facilitate alignment of two or more images of the portion of the subject;
wherein at least a portion of the dental device is positionable within a subject's mouth, and wherein one or more of the radiopaque markers are positioned in the portion of the dental device that is positioned in the subject's mouth during use.

2. The device of claim 1, wherein the device is configured to allow the subject freedom of movement when positioned in the subject's mouth.

3. The device of claim 1, further comprising a grasping device coupled to the dental device.

4. The device of claim 1, wherein the dental device comprises a bite plate.

5. The device of claim 1, wherein the dental device is configured to be reproducibly positioned in the subject's mouth.

6. A method for aligning two or more images of a subject, comprising:
obtaining a dental device wherein the dental device comprises impressions of at least a portion of one or more teeth of a subject;
positioning at least a portion of the dental device in the subject's mouth using the impressions formed in the dental device to position the dental device in a substantially fixed spatial relationship relative to at least a portion of the subject, wherein the dental device comprises one or more radiopaque markers, and wherein one or more of the radiopaque markers are positioned in the portion of the dental device that is positioned in the subject's mouth;
obtaining two or more images of at least the portion of the subject and at least a portion of at least one of the radiopaque markers; and
using at least a portion of an image of at least one of the radiopaque markers as a reference to align at least a part of two or more of the images.

7. The method of claim 6, using at least a portion of at least one of the radiopaque markers as a reference to align at least a part of two or more of the images after the images have been obtained.

8. The method of claim 6, allowing the subject at least a minimum of freedom of movement of at least the portion of the subject relative to an imaging system and relative to a position of the portion of the subject during a plurality of images.

9. The method of claim 6, wherein at least the portion of the subject is in a first position relative to an imaging system when a first image is obtained, wherein at least the portion of the subject is in a second position relative to an imaging system when a second image is obtained, and wherein the first position is different from the second position.

10. The method of claim 6, further comprising using at least a portion of at least one of the radiopaque markers as a reference to align at least a part of two or more of the images such that the images may be compared.

11. The method of claim 6, further comprising using at least a portion of at least one of the radiopaque markers as a reference to align at least a part of two or more images after the images have been obtained such that digital images may be compared in a quantitative manner.

12. The method of claim 6, further comprising using at least a portion of at least one of the radiopaque markers as a reference to align at least a part of two or more images after the images have been obtained such that digital images may be used for digital subtraction radiography analysis.

* * * * *